United States Patent

Kelly et al.

Patent Number: 5,567,349
Date of Patent: Oct. 22, 1996

[54] PHOTO CROSS-LINKABLE LIQUID CRYSTALS

[75] Inventors: Stephen Kelly, Möhlin; Martin Schadt, Seltisberg, both of Switzerland; Klaus Schmitt, Lörrach, Germany

[73] Assignee: Hoffmann-La Roche Inc., Nutley, N.J.

[21] Appl. No.: 396,847

[22] Filed: Mar. 1, 1995

[30] Foreign Application Priority Data

Mar. 30, 1994 [SE] Sweden ................................. 953/94

[51] Int. Cl.$^6$ ................... C09K 19/52; C09K 19/20; C07C 69/76
[52] U.S. Cl. ................... 252/299.01; 252/199.64; 252/299.67; 560/76; 560/85; 560/88
[58] Field of Search ................... 252/299.01, 299.61, 252/299.62, 299.63, 299.64, 299.67; 560/76, 88, 84, 85

[56] References Cited

U.S. PATENT DOCUMENTS

| | | | |
|---|---|---|---|
| 4,801,734 | 1/1989 | Kock et al. | 252/299.64 |
| 5,043,192 | 8/1991 | Jones et al. | 252/299.01 |
| 5,093,471 | 3/1992 | West | 252/299.01 |
| 5,098,975 | 3/1992 | Omelis et al. | 252/299.01 |
| 5,210,630 | 5/1993 | Heynderickx et al. | 252/299.01 |
| 5,385,690 | 1/1995 | Finkelmann et al. | 252/299.01 |

FOREIGN PATENT DOCUMENTS

| | | |
|---|---|---|
| 0254865 | 6/1987 | European Pat. Off. |
| 0501563 | 2/1992 | European Pat. Off. |
| 2182662 | 5/1987 | United Kingdom. |

OTHER PUBLICATIONS

Liquid Crystals, Bd. 14, Nr. 1 1993, London GB Seiten 15–36.

*Primary Examiner*—Shean C. Wu
*Attorney, Agent, or Firm*—George W. Johnston; Ellen Ciambrone Coletti

[57] ABSTRACT

The present invention is concerned with photo cross-linkable liquid crystals of the formula

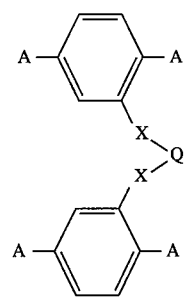

I wherein
A is a cross-linkable mesogenic residue;
X is a single bond, —COO—, —CH$_2$O—, —CONH— or —C=N—; and
Q is n-alkylene, c-alkylene, 1,4-phenylene, 4,4'-biphenylene or 2,6-naphthylene;

liquid crystalline mixtures which contain such compounds as well as their use in the cross-linked state for optical building elements.

6 Claims, No Drawings

$5,567,349$

PHOTO CROSS-LINKABLE LIQUID CRYSTALS

BRIEF SUMMARY OF THE INVENTION

The present invention relates to photo cross-linkable liquid crystals of the formula

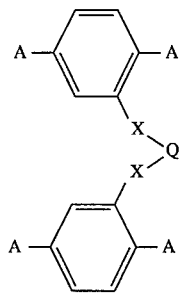

wherein

A is a cross-linkable mesogenic residue;

X is a single bond, —COO—, —CH$_2$O—, —CONH— or —C=N—; and

Q is n-alkylene, c-alkylene, 1,4-phenylene, 4,4'-biphenylene or 2,6-naphthylene;

liquid crystalline mixtures which contain such compounds as well as their use in the cross-linked state for optical building elements.

BACKGROUND OF THE INVENTION

Photo cross-linkable liquid crystals provided with a suitable amount of a photoinitiator can be orientated by an orienting layer on a substrate such as glass or silicon or in an electric or magnetic field and can then be cross-linked by irradiation with light of a suitable wavelength. The thus-produced orientation remains even at high temperatures. This also applies when the orientating layer consists of photo-orientable polymer network layers (PPN) which induce a high resolution orientation pattern on liquid crystal layers by selective radiation with polarized UV light. Such hybrid layers make it possible to transfer the optically registered high resolution orientation structure of a thin polymer layer to a double refractive densely cross-linked polymer layer of any thickness. Mixtures consisting of photo cross-linkable liquid crystals or photo cross-linkable liquid crystals and low molecular liquid crystals and/or optically active (chiral) additives are used depending on the application. Thus, optical building elements having long-term stability, such as, for example, optical retarders, wave guides, optical grids and filters, integrated color filters, piezo-electric optical building elements and those having non-linear optical (NLO) properties, and the like can be manufactured. Such optical building elements find use, for example, in projection systems.

Further properties, such as, for example, the birefringence, the refractive index, the transparency, etc. must fulfil different requirements depending on the field of application. For example, materials for optical retarders should have a high birefringence in order that the layer thickness of the integrated optical building element can be kept to a minimum.

Besides the general interest in photo cross-linkable liquid crystals for optical building elements, such liquid crystalline materials are suitable for cladding glass fibres for optical data transmission. The use of such materials increases the elastic modulus in the longitudinal axis of the fibre, lessens the thermal expansion coefficient and reduces microdistortion losses. This leads to an increased mechanical stability.

The photo cross-linkable liquid crystals must have a good chemical and thermal stability, a good solubility in usual solvents and a good stability towards electric fields and electromagnetic radiation. Furthermore, they should have a suitable mesophase from about 25° C. to about 80° C., when possible from about 25° C. to about 100° C., for example a broad smectic or nematic mesophase and, respectively, a chiral smectic and cholesteric mesophase, for the applications mentioned above.

Since liquid crystals are usually used as mixtures of several components, it is important that the components have a good miscibility with one another.

DESCRIPTION OF THE INVENTION

The present invention now provides compounds which are outstandingly suitable as single components or as components of liquid crystal mixtures for optical building elements as described above. The object of the present invention accordingly comprises compounds of the formula

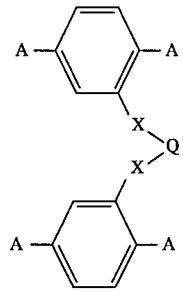

wherein

A is a cross-linkable mesogenic residue;

X is a single bond, —COO—, —CH$_2$O—, —CONH— or —C=N—; and

Q is n-alkylene, c-alkylene, 1,4-phenylene, 4,4'-biphenylene or 2,6-naphthylene.

The compounds of formula I are distinguished by their relatively low viscosity. They can therefore be applied without problems to a suitable surface. Generally, this is carried out by spin-coating. Since, moreover, the compounds in accordance with the invention have a liquid crystalline phase, they can be directed by the application of an electric field prior to the cross-linking. This is especially the case for compounds of formula I in accordance with the invention in which the mesogenic residues A each represent a residue of the formula

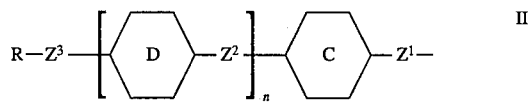

wherein rings C and D each independently are 1,4-phenylene, which is optionally substituted with halogen, methyl and/or cyano, pyridine- 2,5-diyl, pyrimidine-2,5-diyl, trans-1,4 -cyclohexylene or trans-1,3-dioxane-2,5 -diyl;

$Z^1$ is —CH$_2$CH$_2$—, —CH$_2$O—, —COO—, —OOC—, —(CH$_2$)$_4$— or —(CH$_2$)$_3$O—;

$Z^2$ is a single bond, —$CH_2CH_2$—, —$CH_2O$—, —$OCH_2$—, —COO—, —OOC—, —$(CH_2)_4$—, —$O(CH_2)_3$— or —$(CH_2)_3O$—;

$Z^3$ is —$(CH_2)_m$—, —$(CH_2)_mO$—, —$O(CH_2)_m$—, —$(CH_2)_mCOO$—, —$OOC(CH_2)_m$—, —$(CH_2)_mOOC$— or —$COO(CH_2)_m$—;

n is 0 or 1;

m is a whole number of 1 to 16; and

R is a cross-linkable group such as acrylate, methacrylate, 2-chloroacrylate, 2-phenylacrylate, acryloylphenylene, acrylamide, methacrylamide, 2-phenylacrylamide, epoxy, itaconic acid ester, vinyl ether, vinyl ester, styrene derivative, maleic acid derivative, fumaric acid derivative or a cinnamic acid derivative optionally substituted with methyl, methoxy, cyano and/or halogen.

Particularly preferred mesogenic residues are those in which rings C and D each independently signify unsubstituted or fluoro-substituted 1,4-phenylene, pyridine-2,5-diyl, pyrimidine-2,5-diyl or trans-1,4-cyclohexylene; $Z^1$ represents —$CH_2O$—, —COO— or —OOC—; and $Z^2$ signifies —$CH_2CH_2$—, —$CH_2O$—, —$OCH_2$—, —COO— or —OOC—.

As used herein, the term "mesogenic residue" refers to a residue which gives rise to a mesophase.

The term "n-alkylene" signifies in the scope of the present invention a straight-chain alkylene with 1 to 16 carbon atoms. Especially preferred alkylenes are 1,4-butylene, 1,5-pentylene, 1,6-hexylene, 1,7-heptylene, 1,8-octylene, 1,9-nonylene, 1,10-decylene, 1,11-undecylene and 1,12-dodecylene. The term "c-alkylene" stands for a cyclic alkylene with 4 to 8 carbon atoms such as, for example, 1,3-cyclobutylene, 1,2- or 1,3-cyclopentylene, 1,4-cyclohexylene, 1,4-bicylo(2,2,2)octane and the like.

"1,4-Phenylene which is optionally substituted with halogen, methyl and/or cyano," embraces in the present invention 1,4-phenylene, fluoro-, bromo-, chloro-, methyl- or cyano-substituted 1,4-phenylene such as, for example, 2- or 3-fluoro-1,4-phenylene, 1,3-difluoro-1,4-phenylene, 2,6- or 3,5-difluoro-1,4-phenylene, 2- or 3-chioro-1,4-phenylene, 2,3-dichioro-1,4-phenylene, 2,6- or 3,5-dichioro-1,4-phenylene, 2-or 3-bromo-1,4-phenylene, 2- or 3-methyl-1,4-phenylene, 2- or 3-cyano-1,4-phenylene and the like.

Acrylate, methacrylate, 2-chioroacrylate, 2-phenylacrylate, acryloylphenylene, acrylamide, methacrylamide, 2-phenylacrylamide, vinyl ether, vinyl ester, styrene derivative, maleic acid derivative, fumaric acid derivative and the like are preferred residues R. These residues can be cross-linked photochemically after coating the suitable carrier with compounds of formula I.

Acrylate, methacrylate, acryloyloxy, methacryloyloxy, vinyloxy and epoxy are especially preferred residues R.

Preferably, X in compounds of formula I signifies a —COO—, —CONH— or —$CH_2O$— group. These groups are readily accessible from the corresponding aldehyde and can then be reacted ready with a suitable derivative of the group Q, which preferably signifies —$(CH_2)_p$—, wherein p is a whole number between 2 and 12, or 1,4-phenylene.

The mesophase type of the compounds in accordance with the invention can be influenced by varying the rings in the mesogenic side-chain A. Thus, heterocyclic rings have the tendency to produce smectic phases, while cyclohexylene rings promote nematic tendencies. Preferably, these mesogenic residues A signify a residue of formula II in which n=0, such as, for example,

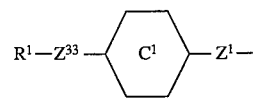

II-a wherein $R^1$ is acrylate, methacrylate, 2-chloroacrylate, 2-phenylacrylate, vinyloxy or epoxy;

$Z^{33}$ is —$(CH_2)_{m'}$—, —$(CH_2)_mO$—, —$(CH_2)_mCOO$— or —$(CH_2)_mOOC$—;

m' is a whole number of 4 to 12;

ring $C^1$ is 1,4-phenylene, which is optionally substituted with halogen, or trans-1,4-cyclohexylene; and $Z^1$ is —$CH_2CH_2$—, —$CH_2O$—, —COO—, —OOC—, —$(CH_2)_4$— or —$(CH_2)_3O$—.

Particularly preferred compounds of formula I are compounds of the formulas

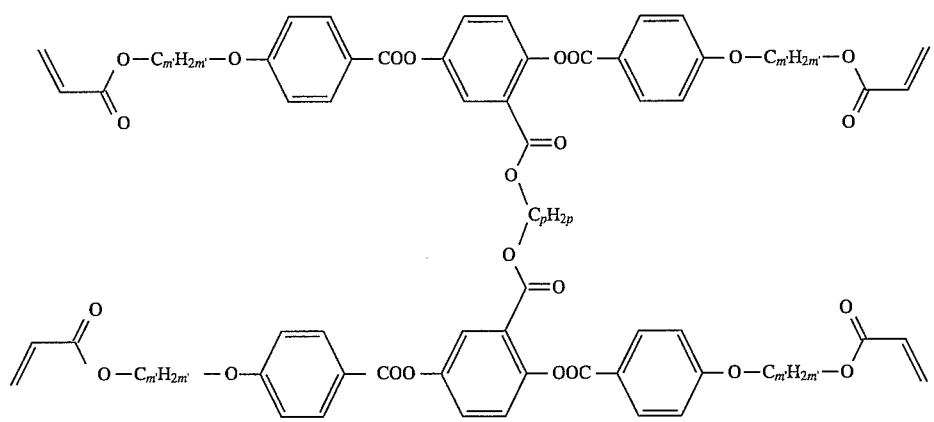

I-a

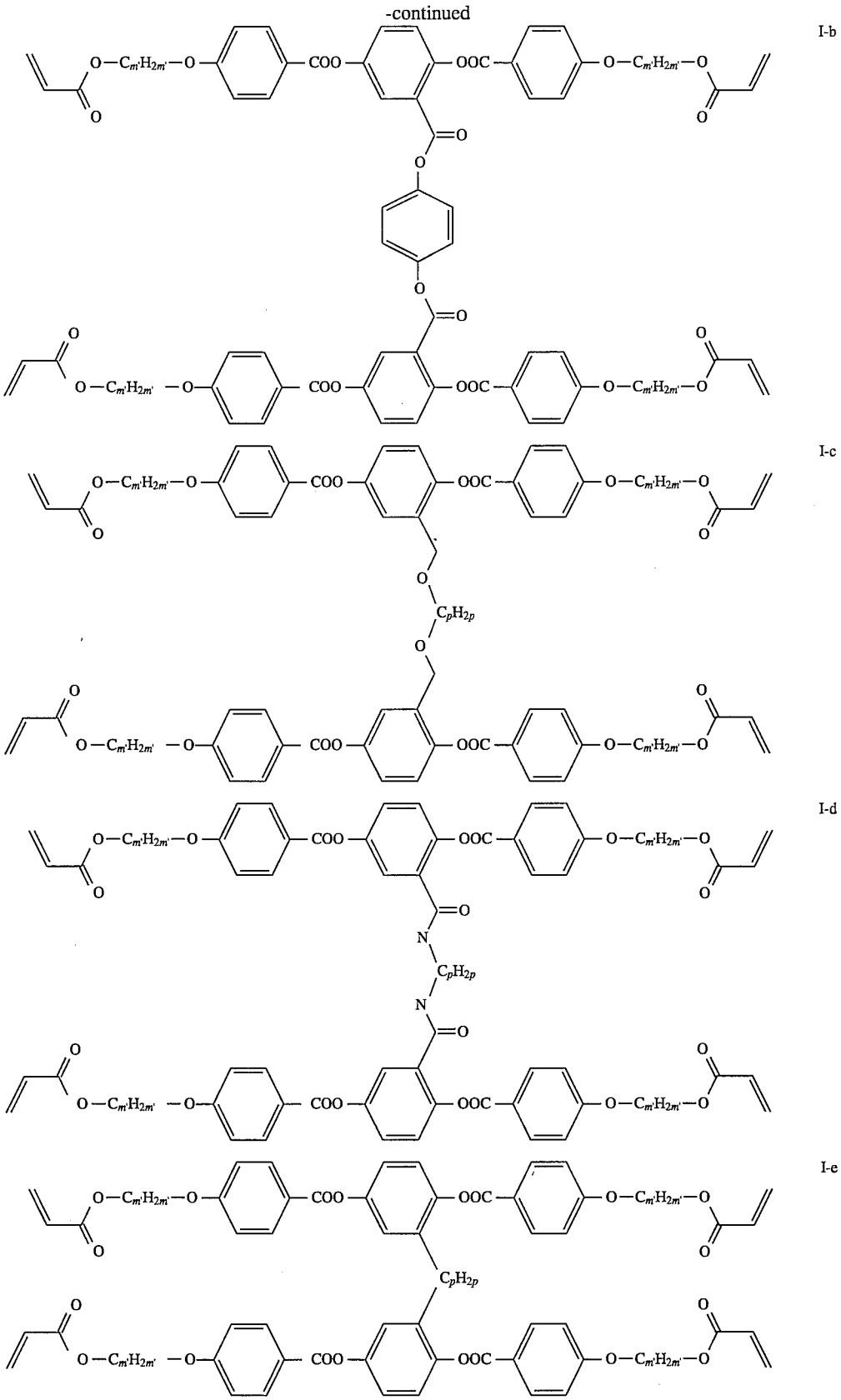

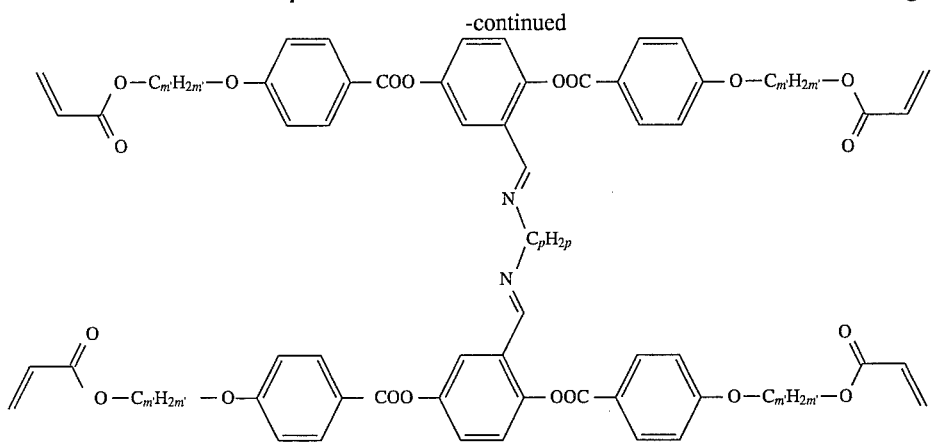
wherein m' signifies a whole number of 4 to 12 and p signifies a whole number of 2 to 12.
The access to the compounds in accordance with the invention is extraordinarily simple. They can be prepared in a known manner as illustrated in Schemes 1–6.
SCHEME 1
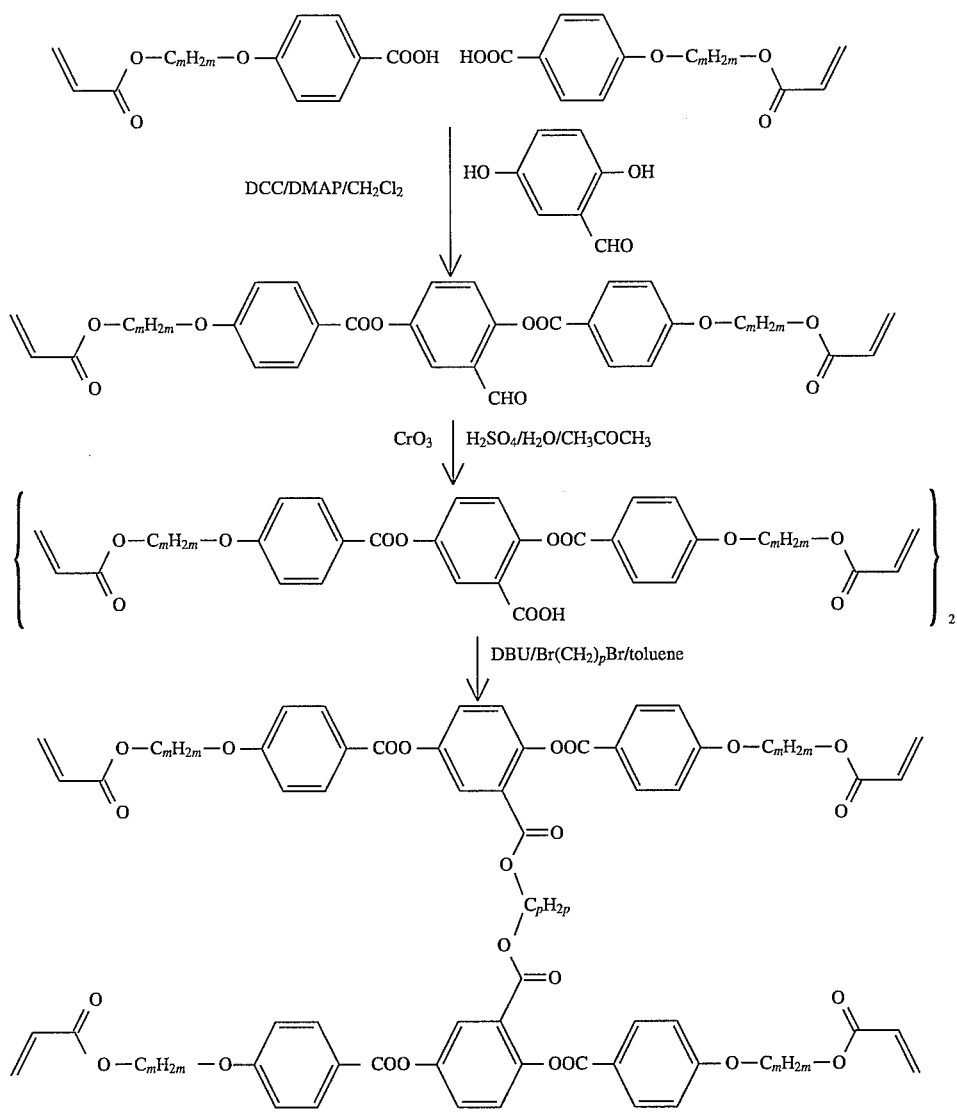

wherein m is a whole number of 1 to 16 and p is a whole number of 2–12.

The diesters shown in Scheme 1 can be prepared by esterification of 2,5-dihydroxybenzaldehyde with 4-[ω-acryloyloxy-alkyloxy]benzoic acids in the presence of N,N'-dicyclohexylcarbodiimide ("DCC") and 4-(dimethylamino)pyridine ("DMAP") in a polar solvent like dichloromethane. Oxidation of the resultant 2,5-bis(4-[ω-acryloyloxyalkyloxy]phenylcarboxy) benzaldehydes with Jones' reagent yields the corresponding benzoic acids, which are alkylated with appropriate ω-dibromoalkanes in the presence of a base like 1,8-diazobicylo[5,4,0]undec-1-ene)1,5-5 ("DBU") to yield the desired diesters.

SCHEME 2

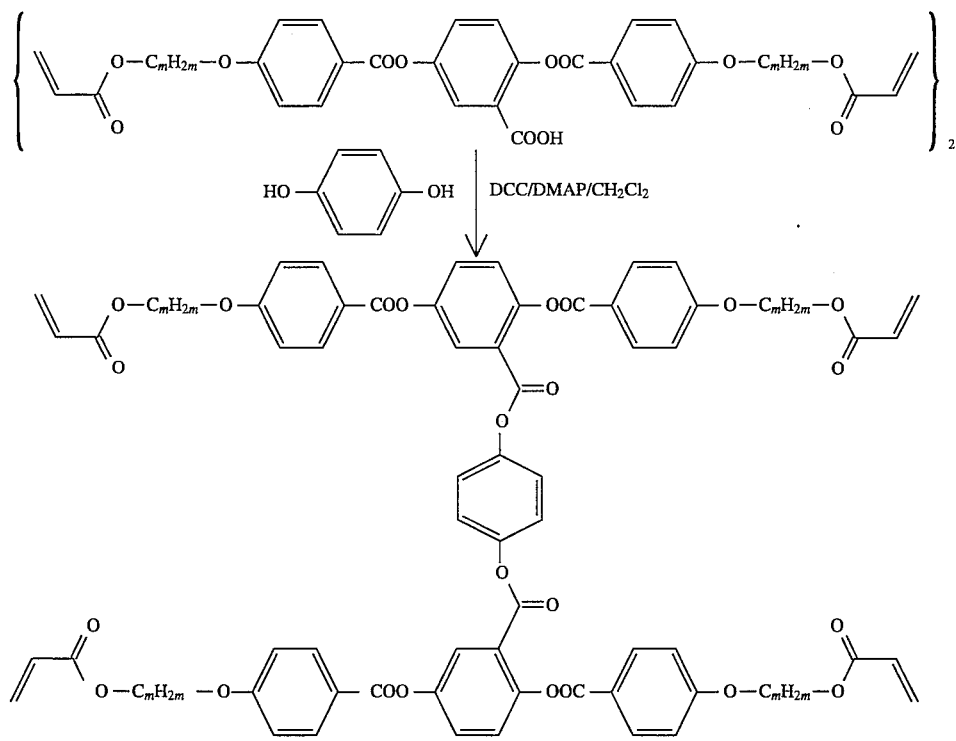

wherein m is a whole number of 1 to 16 and p is a whole number of 2–12.

The diesters shown in Scheme 2 can be prepared by esterification of hydroquinone with 2,5-bis(4-[ω-acryloyloxyalkyloxy]phenylcarboxy)benzoic acids in the presence of N,N'-dicyclohexylcarbodiimide and 4-(dimethylamino)pyridine dichloromethane as above.

SCHEME 3

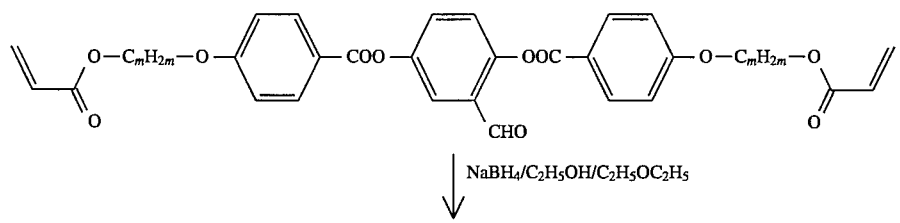

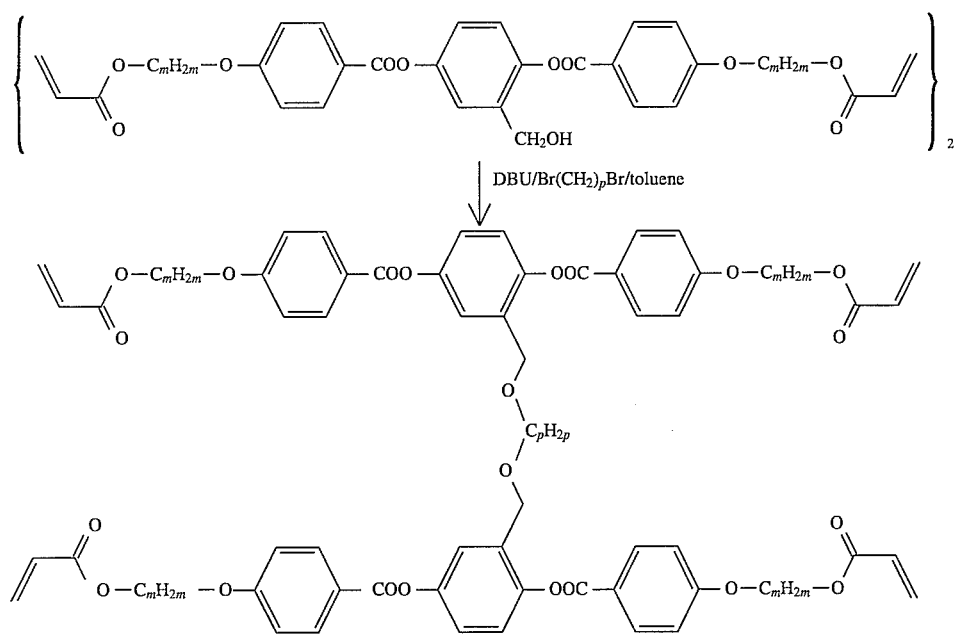

wherein m is a whole number of 1 to 16 and p is a whole number of 2–12.

The diethers shown in Scheme 3 can be prepared by reduction of 2,5-bis(4-[ω-acryloyloxyalkyloxy]phenylcarboxy) benzaldehydes with sodium borohydride to the corresponding 2,5-bis(4-[ω-acryloyloxyalkyloxy]phenylcarboxy)benzyl alcohols followed by alkylation with the appropriate ω-dibromoalkanes in the presence of a base like potassium tert-butoxide and a polar solvent like dimethyl sulfoxide.

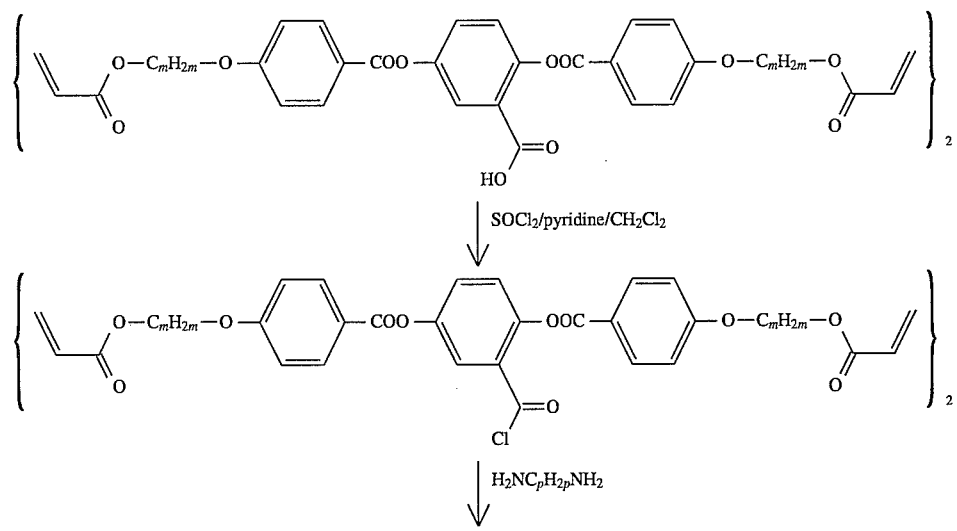

-continued
SCHEME 4

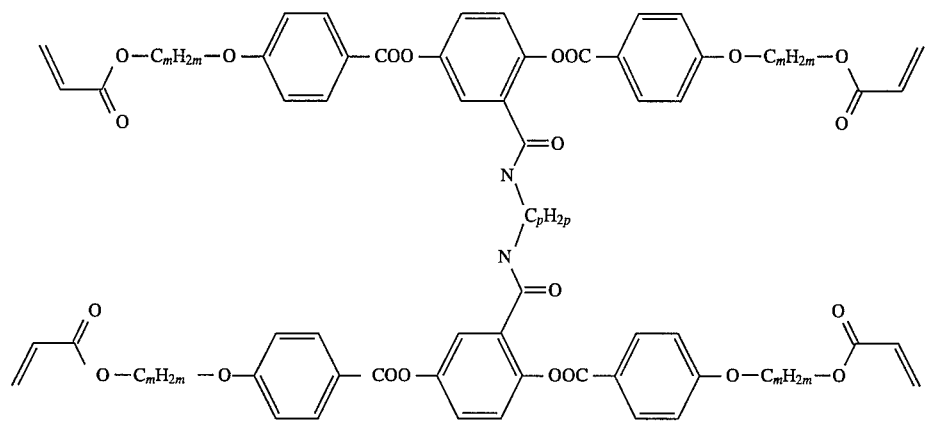

wherein m is a whole number of 1 to 16 and p is a whole number of 2–12.

The diamines shown in Scheme 4 can be prepared by conversion of 2,5-bis(4-[ω-acryloyloxyalkyloxy]phenylcarboxy)benzoic acids with thionyl chloride to the corresponding acid chlorides. Reaction with the appropriate ω-diaminoalkanes in a polar solvent like dichloromethane yields the desired diamides.

The diesters shown in Scheme 5 can be prepared by esterification of 1,5-bis(hydroquinoyl)alkanes with 4-[ω-acryloyloxyalkyloxy]benzoic acids in the presence of N,N'-dicyclohexylcarbodiimide and 4-(dimethylamino)pyridine in dichloromethane as above.

SCHEME 5

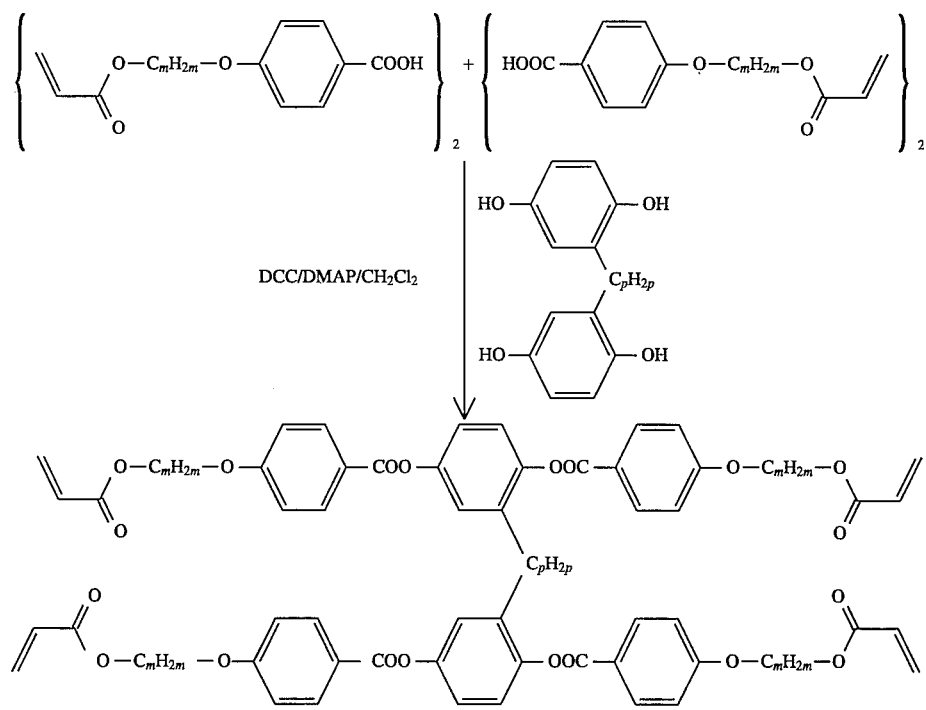

wherein m is a whole number of 1 to 16 and p is a whole number of 2 to 12.

SCHEME 6

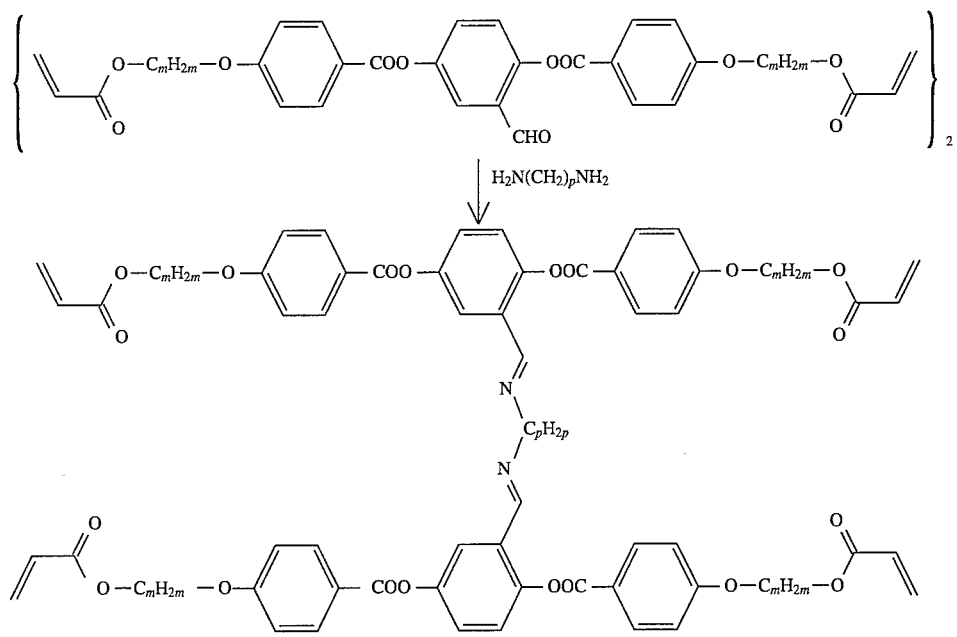

wherein m is a whole number of 1 to 16 and p is a whole number of 2 to 12.

The distilbenes shown in Scheme 6 can be prepared by reaction of 2,5-bis(4-[ω-acryloyloxyalkyloxy]phenylcarboxy) benzaldehydes with the appropriate ω-diaminoalkanes in the presence of a polar solvent like ethanol and a catalytic amount of add.

A small amount of BHT (2,6-di-tert.-butyl-4-methylphenol/"butylhydroxytoluene") is admixed in each step in order to stop undesired thermal cross-linking.

The compounds of formula I can be used as single compounds or in the form of mixtures with one another and/or with other liquid crystal components.

Also, one or more chiral components can be present in the mixture.

Having regard to the good solubility of the compounds of formula I and having regard to their good miscibility with one another, the content of different compounds of formula I in the mixtures in accordance with the invention can be high and can amount to up to 100 wt. %.

Preferably, the mixtures in accordance with the invention comprise, in addition to one or more compounds of formula I, one or more compounds from the group of compounds of the formula

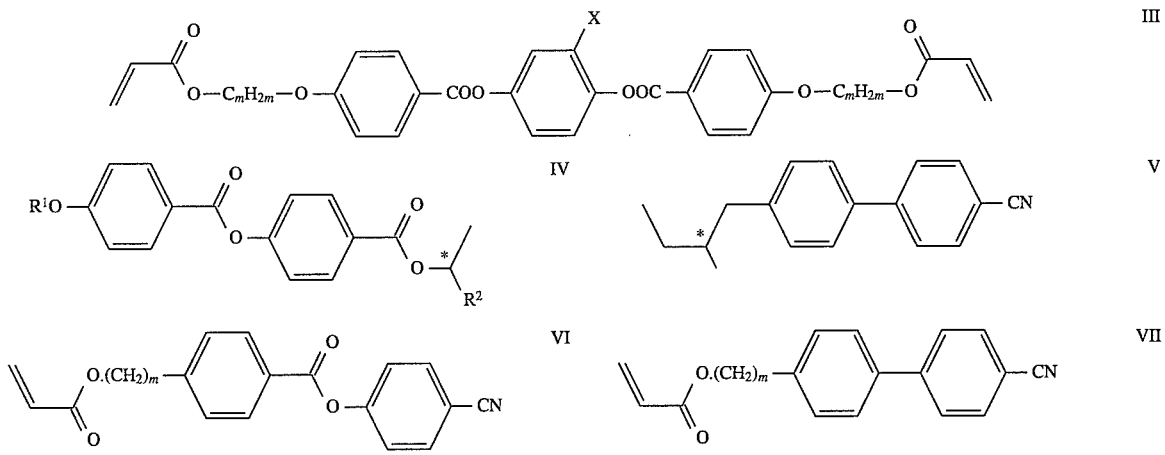

The liquid crystalline mixtures in accordance with the invention comprise at least 2 components, of which at least one component is a compound of formula I. A second component and any other components can be additional compounds of formula I or other known liquid crystal compounds with or without photo cross-linkable groups.

wherein $R^1$ and $R^2$ each independently represent alkyl or alkenyl with 2 to 12 carbon atoms; X represents hydrogen, lower alkyl, fluorine, bromine, chlorine or cyano; and m signifies a whole number of 1 to 16.

The invention is illustrated in more detail by the following Examples. In the Examples C signifies a crystalline phase, N signifies a nematic phase, S signifies a smectic phase and I signifies the isotropic phase.

EXAMPLE 1

0.15 g of DBU (1,8-diazobicylo[5,4,0]undec-1-ene(1,5-5) was added at room temperature while stirring to a solution of 0.7 g of 2,5-bis(4-[6-acryloyloxyhexyloxy)]phenylcarbonyloxy)benzoic acid and 0.11 g of 1,4-dibromobutane in 20 ml of toluene. The reaction mixture was heated at 80° C. overnight, poured into 100 ml of water and then extracted three times with 50 ml of ethyl acetate each time. The combined organic phases were washed twice with 100 ml of water each time, dried over magnesium sulfate, filtered and subsequently concentrated. Chromatographic purification of the residue on silica gel with hexane/ethyl acetate (vol. 2:1) and two-fold recrystallization from acetone of the fractions which were pure according to thin-layer chromatography gave 0.3 g of 1,4-butylene bis[2,5-bis(4-[6 -acryloyloxyhexyloxy)]phenylcarbonyloxy)benzoic acid ester]; m.p. (C-N) 59° C., cl.p. (N-I) 105° C.

The 2,5-bis(4-[6-acryloyloxyhexyloxy)]phenylcarbonyloxy)benzoic acid used as the starting material was prepared as follows:

(a) 29.7 g of N,N'-dicyclohexylcarbodiimide (DCC) were added at 0° C. while stirring within 15 minutes to a solution of 8.3 g of 2,5-dihydroxybenzaldehyde, 35.1 g of 4-[6-acryloyloxyhexyloxy]benzoic acid and 0.1 g of 4-(dimethylamino)pyridine (DMAP) in 600 ml of dichloromethane. The reaction mixture was stirred at room temperature overnight, then filtered and subsequently concentrated. Chromatographic purification of the residue on silica gel with hexane/ethyl acetate (vol. 1:1) and two-fold recrystallization from ethyl alcohol of the fractions which were pure according to thin-layer chromatography gave 7.8 g of 2,5-bis(4-[6-acryloyloxyhexyloxy)]phenylcarbonyloxy)benzaldehyde.

(b) A solution of 3.9 g of 2,5-bis(4-[6-acryloyloxyhexyloxy)]phenylcarbonyloxy)benzaldehyde in 50 ml of acetone was treated dropwise with 18 ml of Jones' reagent. The mixture was stirred at room temperature for 1 hour, poured into 100 ml of water and then extracted three times with 50 ml of ethyl acetate each time. The combined organic phases were washed twice with 100 ml of water each time, dried over magnesium sulfate, filtered and subsequently concentrated. The residue was recrystallized from tert.-butyl methyl ether at −78° C. This gave 2.3 g of 2,5 -bis(4-[6-acryloyloxyhexyloxy)]phenylcarbonyloxy)benzoic acid; m.p. (C-I) 126° C., cl.p. (N-I) 122° C.

The following compounds can be prepared in an analogous manner:

1,5-Pentylene bis[2,5-bis(4-[6-acryloyloxyhexyloxy)]phenylcarbonyloxy)benzoic acid ester]; m.p. (C-N) 62° C., cl.p. (N-I) 96° C.
1,6-Hexylene bis[2,5-bis(4-[6-acryloyloxyhexyloxy)]phenylcarbonyloxy)benzoic acid ester]; m.p. (C-N) 94° C., cl.p. (N-I) 113° C.
1,7-Heptylene bis[2,5-bis(4-[6-acryloyloxyhexyloxy)]phenylcarbonyloxy)benzoic acid ester]; m.p. (C-N) 45° C., cl.p. (N-I) 85° C.
1,8-Octylene bis[2,5-bis(4-[6-acryloyloxyhexyloxy)]phenylcarbonyloxy)benzoic acid ester]; m.p. (C-N) 65° C., cl.p. (N-I) 97° C.
1,9-Nonylene bis[2,5-bis(4-[6-acryloyloxyhexyloxy)]phenylcarbonyloxy)benzoic acid ester].
1,10-Decylene bis[2,5-bis(4-[6-acryloyloxyhexyloxy)]phenylcarbonyloxy)benzoic acid ester].
1,4-Butylene bis[2,5-bis(4-[7-acryloyloxyheptyloxy)]phenylcarbonyloxy)benzoic acid ester].
1,5-Pentylene bis[2,5-bis(4-[7-acryloyloxyheptyloxy)]phenylcarbonyloxy)benzoic acid ester].
1,6-Hexylene bis[2,5-bis(4-[7-acryloyloxyheptyloxy)]phenylcarbonyloxy)benzoic acid ester].
1,7-Heptylene bis[2,5-bis(4-[7-acryloyloxyheptyloxy)]phenylcarbonyloxy)benzoic acid ester].
1,8-Octylene bis[2,5-bis(4-[7-acryloyloxyheptyloxy)]phenylcarbonyloxy)benzoic acid ester].
1,9-Nonylene bis[2,5-bis(4-[7-acryloyloxyheptyloxy)]phenylcarbonyloxy)benzoic acid ester].
1,10-Decylene bis[2,5-bis(4-[7-acryloyloxyheptyloxy)]phenylcarbonyloxy)benzoic acid ester].
1,4-Butylene bis[2,5-bis(4-[8-acryloyloxyoctyloxy)]phenylcarbonyloxy)benzoic acid ester].
1,5-Pentylene bis[2,5-bis(4-[8-acryloyloxyoctyloxy)]phenylcarbonyloxy)benzoic acid ester].
1,6-Hexylene bis[2,5-bis(4-[8-acryloyloxyoctyloxy)]phenylcarbonyloxy)benzoic acid ester].
1,7-Heptylene bis[2,5-bis(4-[8-acryloyloxyoctyloxy)]phenylcarbonyloxy)benzoic acid ester].
1,8-Octylene bis[2,5-bis(4-[8-acryloyloxyoctyloxy)]phenylcarbonyloxy)benzoic acid ester].
1,9-Nonylene bis[2,5-bis(4-[8-acryloyloxyoctyloxy)]phenylcarbonyloxy)benzoic acid ester].
1,10-Decylene bis[2,5-bis(4-[8-acryloyloxyoctyloxy)]phenylcarbonyloxy)benzoic acid ester].
1,4-Butylene bis[2,5-bis(4-[9-acryloyloxynonyloxy)]phenylcarbonyloxy)benzoic acid ester].
1,5-Pentylene bis[2,5-bis(4-[9-acryloyloxynonyloxy)]phenylcarbonyloxy)benzoic acid ester].
1,6-Hexylene bis[2,5-bis(4-[9-acryloyloxynonyloxy)]phenylcarbonyloxy)benzoic acid ester].
1,7-Heptylene bis[2,5-bis(4-[9-acryloyloxynonyloxy)]phenylcarbonyloxy)benzoic acid ester].
1,8-Octylene bis[2,5 -bis(4-[9-acryloyloxynonyloxy)]phenylcarbonyloxy)benzoic acid ester].
1,9-Nonylene bis[2,5-bis(4-[9-acryloyloxynonyloxy)]phenylcarbonyloxy)benzoic acid ester].
1,10-Decylene bis[2,5-bis(4-[9-acryloyloxynonyloxy)]phenylcarbonyloxy)benzoic acid ester].
1,4-Butylene bis[2,5-bis(4-[10-acryloyloxydecyloxy)]phenylcarbonyloxy)benzoic acid ester].
1,5-Pentylene bis[2,5-bis(4-[10-acryloyloxydecyloxy)]phenylcarbonyloxy)benzoic acid ester].
1,6-Hexylene bis[2,5-bis(4-[10-acryloyloxydecyloxy)]phenylcarbonyloxy)benzoic acid ester].
1,7-Heptylene bis[2,5-bis(4-[10-acryloyloxydecyloxy)]phenylcarbonyloxy)benzoic acid ester].
1,8-Octylene bis[2,5-bis(4-[10-acryloyloxydecyloxy)]phenylcarbonyloxy)benzoic acid ester].
1,9-Nonylene bis[2,5-bis(4-[10-acryloyloxydecyloxy)]phenylcarbonyloxy)benzoic acid ester].
1,10-Decylene bis[2,5-bis(4-[10-acryloyloxydecyloxy)] phenylcarbonyloxy)benzoic acid ester].
1,4-Butylene bis[2,5-bis(4-[11-acryloyloxyundecyloxy)] phenylcarbonyloxy)benzoic acid ester].
1,5-Pentylene bis[2,5-bis(4-[11-acryloyloxyundecyloxy)] phenylcarbonyloxy)benzoic acid ester].
1,6-Hexylene bis[2,5-bis(4-[11-acryloyloxyundecyloxy)] phenylcarbonyloxy)benzoic acid ester].
1,7-Heptylene bis[2,5-bis(4-[11-acryloyloxyundecyloxy)] phenylcarbonyloxy)benzoic acid ester].

1,8-Octylene bis[2,5-bis(4-[11-acryloyloxyundecyloxy)]phenylcarbonyloxy)benzoic acid ester].
1,9-Nonylene bis[2,5-bis(4-[11-acryloyloxyundecyloxy)]phenylcarbonyloxy)benzoic acid ester].
1,10-Decylene bis[2,5-bis(4-[11-acryloyloxyundecyloxy)]phenylcarbonyloxy)benzoic acid ester].
1,5-Pentylene bis[2,5-bis(2-fluoro-4-[6-acryloyloxyhexyloxy)]phenylcarbonyloxy)benzoic acid ester].
1,5-Pentylene bis[2,5-bis(2-chloro-4-[6-acryloyloxyhexyloxy)]phenylcarbonyloxy)benzoic acid ester].
1,5-Pentylene bis[2,5-bis(2-bromo-4-[6-acryloyloxyhexyloxy)]phenylcarbonyloxy)benzoic acid ester].
1,5-Pentylene bis[2,5-bis(2-cyano-4-[6-acryloyloxyhexyloxy)]phenylcarbonyloxy)benzoic acid ester].
1,5-Pentylene bis[2,5-bis(2,3-difluoro-4-[6-acryloyloxyhexyloxy)]phenylcarbonyloxy)benzoic acid ester].
1,5-Pentylene bis[2,5-bis(2,3-dichloro-4-[6-acryloyloxyhexyloxy)]phenylcarbonyloxy)benzoic acid ester].
1,5-Pentylene bis[2,5-bis(4-[6-methacryloyloxyhexyloxy)]phenylcarbonyloxy)benzoic acid ester].
1,6-Hexylene bis[2,5-bis(4-[6-methacryloyloxyhexyloxy)]phenylcarbonyloxy)benzoic acid ester].
1,7-Heptylene bis[2,5-bis(4-[6-methacryloyloxyhexyloxy)]phenylcarbonyloxy)benzoic acid ester].
1,8-Octylene bis[2,5-bis(4-[6-methacryloyloxyhexyloxy)]phenylcarbonyloxy)benzoic acid ester].
1,9-Nonylene bis[2,5-bis(4-[6-methacryloyloxyhexyloxy)]phenylcarbonyloxy)benzoic acid ester].
1,10-Decylene bis[2,5-bis(4-[6-methacryloyloxyhexyloxy)]phenylcarbonyloxy)benzoic acid ester].
1,5-Pentylene bis[2,5-bis(2,3-dichloro-4-[6-vinyloxyhexyloxy)]phenylcarbonyloxy)benzoic acid ester].
1,5-Pentylene bis[2,5-bis(4-[6-vinyloxyhexyloxy)]phenylcarbonyloxy)benzoic acid ester].
1,6-Hexylene bis[2,5-bis(4-[6-vinyloxyhexyloxy)]phenylcarbonyloxy)benzoic acid ester].
1,7-Heptylene bis[2,5-bis(4-[6-vinyloxyhexyloxy)]phenylcarbonyloxy)benzoic acid ester].
1,8-Octylene bis[2,5-bis(4-[6-vinyloxyhexyloxy)]phenylcarbonyloxy)benzoic acid ester].
1,9-Nonylene bis[2,5-bis(4-[6-vinyloxyhexyloxy)]phenylcarbonyloxy)benzoic acid ester].
1,10-Decylene bis[2,5-bis(4-[6-vinyloxyhexyloxy)]phenylcarbonyloxy)benzoic acid ester].
1,5-Pentylene bis[2,5-bis(2,3-dichloro-4-[5,6-epoxyhexyloxy)]phenylcarbonyloxy)benzoic acid ester].
1,5-Pentylene bis[2,5-bis(4-[5,6-epoxyhexyloxy)]phenylcarbonyloxy)benzoic acid ester].
1,6-Hexylene bis[2,5-bis(4-[5,6-epoxyhexyloxy)]phenylcarbonyloxy)benzoic acid ester].
1,7-Heptylene bis[2,5-bis(4-[5,6-epoxyhexyloxy)]phenylcarbonyloxy)benzoic acid ester].
1,8-Octylene bis[2,5-bis(4-[5,6-epoxyhexyloxy)]phenylcarbonyloxy)benzoic acid ester].
1,9-Nonylene bis[2,5-bis(4-[5,6-epoxyhexyloxy)]phenylcarbonyloxy)benzoic acid ester].
1,10-Decylene bis[2,5-bis(4-[5,6-epoxyhexyloxy)]phenylcarbonyloxy)benzoic acid ester].

EXAMPLE 2

(a) 29.788 g of N,N'-dicyclohexylcarbodiimide are added at 0° C. while stirring within 15 minutes to a solution of 4.0 g of hydroquinone, 35.1 g of 2,5-bis(4-[6-acryloyloxyhexyloxy)]phenylcarbonyloxy)benzoic acid and 0.1 g of 4-(dimethylamino)pyridine in 600 ml of dichloromethane. The reaction mixture is stirred at room temperature overnight, then filtered and subsequently concentrated. Chromatographic purification of the residue on silica gel with hexane/ethyl acetate (vol. 1:1) and two-fold recrystallization from ethyl alcohol of the fractions which are pure according to thin-layer chromatography gives 7.8 g of 1,4-phenylene bis[2,5-bis(4-[6-acryloyloxyhexyloxy)]phenylcarbonyloxy)benzoic acid ester].

The following compounds can be prepared in an analogous 1,4-Phenylene bis[2,5-bis(4-[7-acryloyloxyheptyloxy)]phenylcarbonyloxy)benzoic acid ester].
1,4-Phenylene bis[2,5-bis(4-[8-acryloyloxyoctyloxy)]phenylcarbonyloxy)benzoic acid ester].
1,4-Phenylene bis[2,5-bis(4-[9-acryloyloxynonyloxy)]phenylcarbonyloxy)benzoic acid ester].
1,4-Phenylene bis[2,5-bis(4-[10-acryloyloxydecyloxy)]phenylcarbonyloxy)benzoic acid ester].
1,4-Phenylene bis[2,5-bis(4-[11-acryloyloxyundecyloxy)]phenylcarbonyloxy)benzoic acid ester].
trans-1,4-Cyclohexyleme bis[2,5-bis(4-[6-acryloyloxyhexyloxy)]phenylcarbonyloxy)benzoic acid ester].
trans-1,4-Cyclohexylene bis[2,5-bis(4-[7-acryloyloxyheptyloxy)]phenylcarbonyloxy)benzoic acid ester].
trans-1,4-Cyclohexylene bis[2,5-bis(4-[8-acryloyloxyoctyloxy)]phenylcarbonyloxy)benzoic acid ester].
trans-1,4-Cyclohexylene bis[2,5-bis(4-[9-acryloyloxynonyloxy)]phenylcarbonyloxy)benzoic acid ester].
trans-1,4-Cyclohexylene bis[2,5-bis(4-[10-acryloyloxydecyloxy)]phenylcarbonyloxy)benzoic acid ester].
trans-1,4-Cyclohexylene bis[2,5-bis(4-[11-acryloyloxyundecyloxy)]phenylcarbonyloxy)benzoic acid ester].
4,4'-Biphenylene bis[2,5-bis(4-[6-acryloyloxyhexyloxy)]phenylcarbonyloxy)benzoic acid ester].
4,4'-Biphenylene bis[2,5-bis(4-[7-acryloyloxyheptyloxy)]phenylcarbonyloxy)benzoic acid ester].
4,4'-Biphenylene bis[2,5-bis(4-[8-acryloyloxyoctyloxy)]phenylcarbonyloxy)benzoic acid ester].
4,4'-Biphenylene bis[2,5-bis(4-[9-acryloyloxynonyloxy)]phenylcarbonyloxy)benzoic acid ester].
4,4'-Biphenylene bis[2,5-bis(4-[10-acryloyloxydecyloxy)]phenylcarbonyloxy)benzoic acid ester].
4,4'-Biphenylene bis[2,5-bis(4-[11-acryloyloxyundecyloxy)]phenylcarbonyloxy)benzoic acid ester].
1,4-Phenylene bis[2,5-bis(4-[6-methacryloyloxyhexyloxy)]phenylcarbonyloxy)benzoic acid ester].
1,4-Phenylene bis[2,5-bis(4-[7-methacryloyloxyheptyloxy)]phenylcarbonyloxy)benzoic acid ester].
1,4-Phenylene bis[2,5-bis(4-[8-methacryloyloxyoctyloxy)]phenylcarbonyloxy)benzoic acid ester].
1,4-Phenylene bis[2,5-bis(4-[9-methacryloyloxynonyloxy)]phenylcarbonyloxy)benzoic acid ester].
1,4-Phenylene bis[2,5-bis(4-[10-methacryloyloxydecyloxy)]phenylcarbonyloxy)benzoic acid ester].
1,4-Phenylene bis[2,5-bis(4-[11-methacryloyloxyundecyloxy)]phenylcarbonyloxy)benzoic acid ester].
1,4-Phenylene bis[2,5-bis(2,3-dichloro-4-[6-vinyloxyhexyloxy)]phenylcarbonyloxy)benzoic acid ester].
1,4-Phenylene bis[2,5-bis(4-[6-vinyloxyhexyloxy)]phenylcarbonyloxy)benzoic acid ester].
1,4-Phenylene bis[2,5-bis(4-[7-vinyloxyheptyloxy)]phenylcarbonyloxy)benzoic acid ester].
1,4-Phenylene bis[2,5-bis(4-[8-acryloyloxyoctyloxy)]phenylcarbonyloxy)benzoic acid ester].
1,4-Phenylene bis[2,5-bis(4-[9-vinyloxynonyloxy)]phenylcarbonyloxy)benzoic acid ester].
1,4-Phenylene bis[2,5-bis(4-[10-vinyloxydecyloxy)]phenylcarbonyloxy)benzoic acid ester].

1,4-Phenylene bis[2,5-bis(4-[11-vinyloxyundecyloxy)]phenylcarbonyloxy)benzoic acid ester].
1,4-Phenylene bis[2,5-bis(2,3-dichloro-4-[5,6 -epoxyhexyloxy)]phenylcarbonyloxy)benzoic acid ester].
1,4-Phenylene bis[2,5-bis(4-[5,6-epoxyhexyloxy)]phenylcarbonyloxy)benzoic acid ester].
1,4-Phenylene bis[2,5-bis(4-[6,7-epoxyheptyloxy)]phenylcarbonyloxy)benzoic acid ester].
1,4-Phenylene bis[2,5-bis(4-[7,8-epoxyoctyloxy)]phenylcarbonyloxy)benzoic acid ester].
1,4-Phenylene bis[2,5-bis(4-[8,9-epoxynonyloxy)]phenylcarbonyloxy)benzoic acid ester].
1,4-Phenylene bis[2,5-bis(4-[9,10-epoxydecyloxy)]phenylcarbonyloxy)benzoic acid ester].
1,4-Phenylene bis[2,5-bis(4-[10,11-epoxyundecyloxy)]phenylcarbonyloxy)benzoic acid ester].

EXAMPLE 3

0.15 g of potassium tert.-butoxide is added at room temperature while stirring to a solution of 0.7 g of 2,5-bis(4-[6 -acryloyloxyhexyloxy)]phenylcarbonyloxy)benzyl alcohol and 0.11 g of 1,4-dibromobutane in 20 ml of dimethyl sulphoxide. The reaction mixture is stirred at room temperature overnight, poured into 100 ml of water and then extracted three times with 50 ml of ethyl acetate each time. The combined organic phases are washed twice with 100 ml of water each time, dried over magnesium sulfate, filtered and subsequently concentrated. Chromatographic purification of the residue on silica gel with hexane/ethyl acetate (vol. 2:1) and two-fold recrystallization from acetone of the fractions which are pure according to thin-layer chromatography gives 0.3 g of 1,4-butylene bis[2,5-bis(4-[6 -acryloyloxyhexyloxy)]phenylcarbonyloxy)benzyl ether].

The 2,5-bis(4-[6-acryloyloxyhexyloxy)]phenylcarbonyloxy)benzyl alcohol used as the starting material is prepared as follows:

(a) A mixture of 32 g of sodium borohydride and 180 ml of ethanol is treated with 165 ml of water at 0° C., stirred for a further 10 minutes, then treated dropwise at 0°–5° C. with a solution of 50 g of 2,5-bis(4-[6-acryloxyhexyloxy)]phenylcarbonyloxy)benzaldehyde in 100 ml of ethanol and 10 ml of dichloromethane. The reaction mixture is stirred at 0° C. for a further 30 minutes, then poured into 100 ml of dichloromethane and extracted twice with 50 ml of dichloromethane each time. The combined organic phases are then washed twice with 100 ml of water each time, dried over magnesium sulfate, filtered and the filtrate is concentrated. The residue is recrystallized from tert.butyl methyl ether. This gives 35 g of 2,5-bis(4-[6-acryloyloxyhexyloxy)]phenylcarbonyloxy)benzyl alcohol.

The following compounds can be prepared in an analogous
1,5-Pentylene bis[2,5-bis(4-[6-acryloyloxyhexyloxy)]phenylcarbonyloxy)benzyl ether].
1,6-Hexylene bis[2,5-bis(4-[6-acryloyloxyhexyloxy)]phenylcarbonyloxy)benzyl ether].
1,7-Heptylene bis[2,5-bis(4-[6-acryloyloxyhexyloxy)]phenylcarbonyloxy)benzyl ether].
1,8-Octylene bis[2,5-bis(4-[6-acryloyloxyhexyloxy)]phenylcarbonyloxy)benzyl ether].
1,9-Nonylene bis[2,5-bis(4-[6-acryloyloxyhexyloxy)]phenylcarbonyloxy)benzyl ether].
1,10-Decylene bis[2,5-bis(4-[6-acryloyloxyhexyloxy)]phenylcarbonyloxy)benzyl ether].
1,4-Butylene bis[2,5-bis(4-[7-acryloyloxyheptyloxy)]phenylcarbonyloxy)benzyl ether].
1,5-Pentylene bis[2,5-bis(4-[7-acryloyloxyheptyloxy)]phenylcarbonyloxy)benzyl ether].
1,6-Hexylene bis[2,5-bis(4-[7-acryloyloxyheptyloxy)]phenylcarbonyloxy)benzyl ether].
1,7-Heptylene bis[2,5-bis(4-[7-acryloyloxyheptyloxy)]phenylcarbonyloxy)benzyl ether].
1,8-Octylene bis[2,5-bis(4-[7-acryloyloxyheptyloxy)]phenylcarbonyloxy)benzyl ether].
1,9-Nonylene bis[2,5-bis(4-[7-acryloyloxyheptyloxy)]phenylcarbonyloxy)benzyl ether].
1,10-Decylene bis[2,5-bis(4-[7-acryloyloxyheptyloxy)]phenylcarbonyloxy)benzyl ether].
1,4-Butylene bis[2,5-bis(4-[8-acryloyloxyoctyloxy)]phenylcarbonyloxy)benzyl ether].
1,5-Pentylene bis[2,5-bis(4-[8-acryloyloxyoctyloxy)]phenylcarbonyloxy)benzyl ether].
1,6-Hexylene bis[2,5-bis(4-[8-acryloyloxyoctyloxy)]phenylcarbonyloxy)benzyl ether].
1,7-Heptylene bis[2,5-bis(4-[8-acryloyloxyoctyloxy)]phenylcarbonyloxy)benzyl ether].
1,8-Octylene bis[2,5-bis(4-[8-acryloyloxyoctyloxy)]phenylcarbonyloxy)benzyl ether].
1,9-Nonylene bis[2,5-bis(4-[8-acryloyloxyoctyloxy)]phenylcarbonyloxy)benzyl ether].
1,10-Decylene bis[2,5-bis(4-[8-acryloyloxyoctyloxy)]phenylcarbonyloxy)benzyl ether].
1,4-Butylene bis[2,5-bis(4-[9-acryloyloxynonyloxy)]phenylcarbonyloxy)benzyl ether].
1,5-Pentylene bis[2,5-bis(4-[9-acryloyloxynonyloxy)]phenylcarbonyloxy)benzyl ether].
1,6-Hexylene bis[2,5-bis(4-[9-acryloyloxynonyloxy)]phenylcarbonyloxy)benzyl ether].
1,7-Heptylene bis[2,5-bis(4-[9-acryloyloxynonyloxy)]phenylcarbonyloxy)benzyl ether].
1,8-Octylene bis[2,5-bis(4-[9-acryloyloxynonyloxy)]phenylcarbonyloxy)benzyl ether].
1,9-Nonylene bis[2,5-bis(4-[9-acryloyloxynonyloxy)]phenylcarbonyloxy)benzyl ether].
1,10-Decylene bis[2,5-bis(4-[9-acryloyloxynonyloxy)]phenylcarbonyloxy)benzyl ether].
1,4-Butylene bis[2,5-bis(4-[10-acryloyloxydecyloxy)]phenylcarbonyloxy)benzyl ether].
1,5-Pentylene bis[2,5-bis(4-[10-acryloyloxydecyloxy)]phenylcarbonyloxy)benzyl ether].
1,6-Hexylene bis[2,5-bis(4-[10-acryloyloxydecyloxy)]phenylcarbonyloxy)benzyl ether].
1,7-Heptylene bis[2,5 -bis(4-[10-acryloyloxydecyloxy)] phenylcarbonyloxy)benzyl ether].
1,8-Octylene bis[2,5-bis(4-[10-acryloyloxydecyloxy)]phenylcarbonyloxy)benzyl ether].
1,9-Nonylene bis[2,5-bis(4-[10-acryloyloxydecyloxy)]phenylcarbonyloxy)benzyl ether].
1,10-Decylene bis[2,5-bis(4-[10-acryloyloxydecyloxy)] phenylcarbonyloxy)benzyl ether].
1,4-Butylene bis[2,5-bis(4-[11-acryloyloxyundecyloxy)] phenylcarbonyloxy)benzyl ether].
1,5-Pentylene bis[2,5-bis(4-[11-acryloyloxyundecyloxy)] phenylcarbonyloxy)benzyl ether].
1,6-Hexylene bis[2,5-bis(4-[11-acryloyloxyundecyloxy)] phenylcarbonyloxy)benzyl ether].
1,7-Heptylene bis[2,5-bis(4-[11-acryloyloxyundecyloxy)] phenylcarbonyloxy)benzyl ether].
1,8-Octylene bis[2,5-bis(4-[11-acryloyloxyundecyloxy)] phenylcarbonyloxy)benzyl ether].
1,9-Nonylene bis[2,5-bis(4-[11-acryloyloxyundecyloxy)] phenylcarbonyloxy)benzyl ether].

1,10-Decylene bis[2,5-bis(4-[11-acryloyloxyundecyloxy)]phenylcarbonyloxy)benzyl ether].
1,5-Pentylene bis[2,5-bis(4-[6-methacryloyloxyhexyloxy)]phenylcarbonyloxy)benzyl ether].
1,6-Hexylene bis[2,5-bis(4-[6-methacryloyloxyhexyloxy)]phenylcarbonyloxy)benzyl ether].
1,7-Heptylene bis[2,5-bis(4-[6-methacryloyloxyhexyloxy)]phenylcarbonyloxy)benzyl ether].
1,8-Octylene bis[2,5-bis(4-[6-methacryloyloxyhexyloxy)]phenylcarbonyloxy)benzyl ether].
1,9-Nonylene bis[2,5-bis(4-[6-methacryloyloxyhexyloxy)]phenylcarbonyloxy)benzyl ether].
1,10-Decylene bis[2,5-bis(4-[6-methacryloyloxyhexyloxy)]phenylcarbonyloxy)benzyl ether].
1,5-Pentylene bis[2,5-bis(4-[6-vinyloxyhexyloxy)]phenylcarbonyloxy)benzyl ether].
1,6-Hexylene bis[2,5-bis(4-[6-vinyloyloxyhexyloxy)]phenylcarbonyloxy)benzyl ether].
1,7-Heptylene bis[2,5-bis(4-[6-vinyloyloxyhexyloxy)]phenylcarbonyloxy)benzyl ether].
1,8-Octylene bis[2,5-bis(4-[6-vinyloyloxyhexyloxy)]phenylcarbonyloxy)benzyl ether].
1,9-Nonylene bis[2,5-bis(4-[6-vinyloyloxyhexyloxy)]phenylcarbonyloxy)benzyl ether].
1,10-Decylene bis[2,5-bis(4-[6-vinyloyloxyhexyloxy)]phenylcarbonyloxy)benzyl ether].

EXAMPLE 4

A solution of 0.7 g of 2,5-bis(4-[6-acryloyloxyhexyloxy)] phenylcarbonyloxy)benzoyl chloride and 20 ml of dichloromethane is added dropwise at room temperature while stirring to a solution of 0.11 g of 1,4-diaminobutane in 20 ml of dichloromethane. The reaction mixture is stirred at room temperature overnight, poured into 100 ml of water and then extracted three times with 50 ml of ethyl acetate each time. The combined organic phases are washed twice with 100 ml of water each time, dried over magnesium sulfate, filtered and subsequently concentrated. Chromatographic purification of the residue on silica gel with hexane/ethyl acetate (vol. 2:1) and two-fold recrystallization from acetone of the fractions which are pure according to thin-layer chromatography gives 0.3 g of 1,4-butylene bis[2,5-bis(4-[6-acryloyloxyhexyloxy)]phenylcarbonyloxy)benzamide].

The 2,5-bis(4-[6-acryloyloxyhexyloxy)]phenylcarbonyloxy)benzoyl chloride used as the starting material is prepared as follows:

(a) 1.5 g of 2,5-bis(4-[6-acryloxyhexyloxy))]phenylcarbonyloxy)benzoic acid are heated at 80° C. for 2 hours with 25 ml of thionyl chloride in 100 ml of toluene. The solution obtained is evaporated under reduced pressure, the residue is treated with 20 ml of absolute toluene and the solution is again evaporated under reduced pressure. The residue is used in the next step without further purification.

The following compounds can be prepared in an analogous
1,5-Pentylene bis[2,5-bis(4-[6-acryloxyhexyloxy))]phenylcarbonyloxy)benzamide].
1,6-Hexylene bis[2,5-bis(4-[6-acryloxyhexyloxy))]phenylcarbonyloxy)benzamide].
1,7-Heptylene bis[2,5-bis(4-[6-acryloxyhexyloxy))]phenylcarbonyloxy)benzamide].
1,8-Octylene bis[2,5-bis(4-[6-acryloxyhexyloxy))]phenylcarbonyloxy)benzamide].
1,9-Nonylene bis[2,5-bis(4-[6-acryloxyhexyloxy))]phenylcarbonyloxy)benzamide].
1,10-Decylene bis[2,5-bis(4-[6-acryloxyhexyloxy))]phenylcarbonyloxy)benzamide].
1,4-Butylene bis[2,5-bis(4-[7-acryloyloxyheptyloxy))]phenylcarbonyloxy)benzamide].
1,5-Pentylene bis[2,5-bis(4-[7-acryloyloxyheptyloxy))]phenylcarbonyloxy)benzamide].
1,6-Hexylene bis[2,5-bis(4-[7-acryloyloxyheptyloxy))]phenylcarbonyloxy)benzamide].
1,7-Heptylene bis[2,5-bis(4-[7-acryloxyheptyloxy))]phenylcarbonyloxy)benzamide].
1,8-Octylene bis[2,5-bis(4-[7-acryloxyheptyloxy))]phenylcarbonyloxy)benzamide].
1,9-Nonylene bis[2,5-bis(4-[7-acryloyloxyheptyloxy))]phenylcarbonyloxy)benzamide].
1,10-Decylene bis[2,5-bis(4-[7-acryloyloxyheptyloxy))]phenylcarbonyloxy)benzamide].
1,4-Butylene bis[2,5-bis(4-[8-acryloyloxyoctyloxy))]phenylcarbonyloxy)benzamide].
1,5-Pentylene bis[2,5-bis(4-[8-acryloyloxyoctyloxy))]phenylcarbonyloxy)benzamide].
1,6-Hexylene bis[2,5-bis(4-[8-acryloyloxyoctyloxy))]phenylcarbonyloxy)benzamide].
1,7-Heptylene bis[2,5-bis(4-[8-acryloyloxyoctyloxy))]phenylcarbonyloxy)benzamide].
1,8-Octylene bis[2,5-bis(4-[8-acryloyloxyoctyloxy))]phenylarbonyloxy)benzamide].
1,9-Nonylene bis[2,5-bis(4-[8-acryloyloxyoctyloxy))]phenylcarbonyloxy)benzamide].
1,10-Decylene bis[2,5-bis(4-[8-acryloyloxyoctyloxy))]phenylcarbonyloxy)benzamide].
1,4-Butylene bis[2,5-bis(4-[9-acryloyloxynonyloxy))]phenylcarbonyloxy)benzamide].
1,5-Pentylene bis[2,5-bis(4-[9-acryloyloxynonyloxy))]phenylcarbonyloxy)benzamide].
1,6-Hexylene bis[2,5-bis(4-[9-acryloyloxynonyloxy))]phenylcarbonyloxy)benzamide].
1,7-Heptylene bis[2,5-bis(4-[9-acryloyloxynonyloxy))]phenylcarbonyloxy)benzamide].
1,8-Octylene bis[2,5-bis(4-[9-acryloyloxynonyloxy))]phenylarbonyloxy)benzamide].
1,9-Nonylene bis[2,5-bis(4-[9-acryloyloxynonyloxy))]phenylcarbonyloxy)benzamide].
1,10-Decylene bis[2,5-bis(4-[9-acryloyloxynonyloxy))]phenylcarbonyloxy)benzamide].
1,4-Butylene bis[2,5-bis(4-[10-acryloyloxydecyloxy))]phenylcarbonyloxy)benzamide].
1,5-Pentylene bis[2,5-bis(4-[10-acryloyloxydecyloxy))]phenylcarbonyloxy)benzamide].
1,6-Hexylene bis[2,5-bis(4-[10-acryloyloxydecyloxy))]phenylcarbonyloxy)benzamide].
1,7-Heptylene bis[2,5-bis(4-[10-acryloyloxydecyloxy))]phenylcarbonyloxy)benzamide].
1,8-Octylene bis[2,5-bis(4-[10-acryloyloxydecyloxy))]phenylcarbonyloxy)benzamide].
1,9-Nonylene bis[2,5-bis(4-[10-acryloyloxydecyloxy))]phenylcarbonyloxy)benzamide].
1,10-Decylene bis[2,5-bis(4-[10-acryloyloxydecyloxy))]phenylcarbonyloxy)benzamide].
1,4-Butylene bis[2,5-bis(4-[11-acryloyloxyundecyloxy))]phenylcarbonyloxy)benzamide].
1,5-Pentylene bis[2,5-bis(4-[11-acryloyloxyundecyloxy))]phenylcarbonyloxy)benzamide].
1,6-Hexylene bis[2,5-bis(4-[11-acryloyloxyundecyloxy))]phenylcarbonyloxy)benzamide].
1,7-Heptylene bis[2,5-bis(4-[11-acryloyloxyundecyloxy))]phenylcarbonyloxy)benzamide].
1,8-Octylene bis[2,5-bis(4-[11-acryloyloxyundecyloxy))]phenylcarbonyloxy)benzamide].

1,9-Nonylene bis[2,5-bis(4-[11-acryloyloxyundecyloxy)]phenylcarbonyloxy)benzamide].

1,10-Decylene bis[2,5-bis(4-[11-acryloyloxyundecyloxy)]phenylcarbonyloxy)benzamide].

EXAMPLE 5

(a) 29.7 g of N,N'-dicyclohexylcarbodiimide are added at 0° C. while stirring within 15 minutes to a solution of 4.0 g of 1,5-bis(hydroquinoyl)pentane, 35.1 g of 4-[6-acryloyloxyhexyloxy]benzoic acid and 0.1 g of 4-(dimethylamino)pyridine in 600 ml of dichloromethane. The reaction mixture is stirred at room temperature overnight, then filtered and subsequently concentrated. Chromatographic purification of the residue on silica gel with hexane/ethyl acetate (vol. 1:1) and two-fold recrystallization from ethyl alcohol of the fractions which are pure according to thin-layer chromatography gives 7.8 g of 1,5-bis[2,5 -bis(4-[6-acryloyloxyhexyloxy)]phenylcarbonyloxy)phenyl]pentane.

The following compounds can be prepared in an analogous manner:

1,6-Bis[2,5-bis(4-[6-acryloyloxyhexyloxy)]phenylcarbonyloxy)phenyl]hexane.
1,7-Bis[2,5-bis(4-[6-acryloyloxyhexyloxy)]phenylcarbonyloxy)phenyl]heptane.
1,8-Bis[2,5-bis(4-[6-acryloyloxyhexyloxy)]phenylcarbonyloxy)phenyl]octane.
1,9-Bis[2,5-bis(4-[6-acryloyloxyhexyloxy)]phenylcarbonyloxy)phenyl]nonane.
1,10-Bis[2,5-bis(4-[6-acryloyloxyhexyloxy)]phenylcarbonyloxy)phenyl]decane.
1,6-Bis[2,5-bis(4-[7-acryloyloxyheptyloxy)]phenylcarbonyloxy)phenyl]hexane.
1,7-Bis[2,5-bis(4-[7-acryloyloxyheptyloxy)]phenylcarbonyloxy)phenyl]heptane.
1,8-Bis[2,5-bis(4-[7-acryloyloxyheptyloxy)]phenylcarbonyloxy)phenyl]octane.
1,9-Bis[2,5-bis(4-[7-acryloyloxyheptyloxy)]phenylcarbonyloxy)phenyl]nonane.
1,10-Bis[2,5-bis(4-[7-acryloyloxyheptyloxy)]phenylcarbonyloxy)phenyl]decane.
1,6-Bis[2,5-bis(4-[8-acryloyloxyoctyloxy)]phenylcarbonyloxy)phenyl]hexane.
1,7-Bis[2,5-bis(4-[8-acryloyloxyoctyloxy)]phenylcarbonyloxy)phenyl]heptane.
1,8-Bis[2,5-bis(4-[8-acryloyloxyoctyloxy)]phenylcarbonyloxy)phenyl]octane.
1,9-Bis[2,5-bis(4-[8-acryloyloxyoctyloxy)]phenylcarbonyloxy)phenyl]nonane.
1,10-Bis[2,5 -bis(4-[8-acryloyloxyoctyloxy)]phenylcarbonyloxy)phenyl]decane.
1,6-Bis[2,5-bis(4-[9-acryloyloxynonyloxy)]phenylcarbonyloxy)phenyl]hexane.
1,7-Bis[2,5-bis(4-[9-acryloyloxynonyloxy)]phenylcarbonyloxy)phenyl]heptane.
1,8-Bis[2,5-bis(4-[9-acryloyloxynonyloxy)]phenylcarbonyloxy)phenyl]octane.
1,9-Bis[2,5-bis(4-[9-acryloyloxynonyloxy)]phenylcarbonyloxy)phenyl]nonane.
1,10-Bis[2,5-bis(4-[9-acryloyloxynonyloxy)]phenylcarbonyloxy)phenyl]decane.
1,6-Bis[2,5-bis(4-[10-acryloyloxydecyloxy)]phenylcarbonyloxy)phenyl]hexane.
1,7-Bis[2,5-bis(4-[10-acryloyloxydecyloxy)]phenylcarbonyloxy)phenyl]heptane.
1,8-Bis[2,5-bis(4-[10-acryloyloxydecyloxy)]phenylcarbonyloxy)phenyl]octane.
1,9-Bis[2,5-bis(4-[10-acryloyloxydecyloxy)]phenylcarbonyloxy)phenyl]nonane.
1,10-Bis[2,5-bis(4-[10-acryloyloxydecyloxy)]phenylcarbonyloxy)phenyl]decane.
1,6-Bis[2,5-bis(4-[11-acryloyloxyundecyloxy)]phenylcarbonyloxy)phenyl]hexane.
1,7-Bis[2,5-bis(4-[11-acryloyloxyundecyloxy)]phenylcarbonyloxy)phenyl]heptane.
1,8-Bis[2,5-bis(4-[11-acryloyloxyundecyloxy)]phenylcarbonyloxy)phenyl]octane.
1,9-Bis[2,5-bis(4-[11-acryloyloxyundecyloxy)]phenylcarbonyloxy)phenyl]nonane.
1,10-Bis [2,5-bis(4-[11-acryloyloxyundecyloxy)]phenylcarbonyloxy)phenyl]decane.
1,6-Bis[2,5-bis(4-[6-methacryloyloxyhexyloxy)]phenylcarbonyloxy)phenyl]hexane.
1,7-Bis[2,5-bis(4-[6-methacryloyloxyhexyloxy)]phenylcarbonyloxy)phenyl]heptane.
1,8-Bis[2,5-bis(4-[6-methacryloyloxyhexyloxy)]phenylcarbonyloxy)phenyl]octane.
1,9-Bis[2,5-bis(4-[6-methacryloyloxyhexyloxy)]phenylcarbonyloxy)phenyl]nonane.
1,10-Bis[2,5-bis(4-[6-methacryloyloxyhexyloxy)]phenylcarbonyloxy)phenyl]decane.
1,6-Bis[2,5-bis(4-[6-acryloyloxyhexyloxy)]phenylcarbonyloxy)phenyl]hexane.
1,7-Bis[2,5-bis(4-[6-vinyloxyhexyloxy)]phenylcarbonyloxy)phenyl]heptane.
1,8-Bis[2,5-bis(4-[6-vinyloxyhexyloxy)]phenylcarbonyloxy)phenyl]octane.
1,9-Bis[2,5-bis(4-[6-vinyloxyhexyloxy)]phenylcarbonyloxy)phenyl]nonane.
1,10-Bis[2,5-bis(4-[6-vinyloxyhexyloxy)]phenylcarbonyloxy)phenyl]decane.
1,6-Bis[2,5-bis(4-[5,6-epoxyhexyloxy)]phenylcarbonyloxy)phenyl]hexane.
1,7-Bis[2,5-bis(4-[5,6-epoxyhexyloxy)]phenylcarbonyloxy)phenyl]heptane.
1,8-Bis[2,5-bis(4-[5,6-epoxyhexyloxy)]phenylcarbonyloxy)phenyl]octane.
1,9-Bis[2,5-bis(4-[5,6-epoxyhexyloxy)]phenylcarbonyloxy)phenyl]nonane.
1,10-Bis[2,5-bis(4-[5,6-epoxyhexyloxy)]phenylcarbonyloxy)phenyl]decane.

EXAMPLE 6

5 drops of glacial acetic acid are added while stirring and under slight reflux to a solution of 0.7 g of 2,5-bis(4-[6 -acryloyloxyhexyloxy)]phenylcarbonyloxy)benzaldehyde and 0.15 g of 1,5-diaminopentane in 20 ml of ethyl alcohol. After 10 minutes, the reaction mixture is concentrated. Chromatographic purification of the residue on silica gel with hexane/ethyl acetate (vol. 2:1) and two-fold recrystallization from acetone from the fractions which are pure according to thin-layer chromatography gives 0.3 g of 1,5-bis[2,5-bis(4-[6-acryloyloxyhexyloxy)]phenylcarbonyloxy)benzylidene]pentyldiamine.

The following compounds can be prepared in an analogous manner:

1,6-Bis [2,5 -bis(4-[6-acryloyloxyhexyloxy)]phenylcarbonyloxy)benzylidene]hexyldiamine.
1,7-Bis[2,5-bis(4-[6-acryloyloxyhexyloxy)]phenylcarbonyloxy)benzylidene]heptyldiamine.
1,8-Bis[2,5-bis(4-[6-acryloyloxyhexyloxy)]phenylcarbonyloxy)benzylidene]octyldiamine.

1,9-Bis [2,5 -bis(4-[6-acryloyloxyhexyloxy)]phenylcarbonyloxy)benzylidene]nonyldiamine.

1,10-Bis[2,5-bis(4-[6-acryloyloxyhexyloxy)]phenylcarbonyloxy)benzylidene]decyldiamine.

EXAMPLE 7

1,6-Hexylene bis[2,5-bis(4-[6-acryloyloxyhexyloxy)]phenylcarbonyloxy)benzoic acid ester] was treated with 1 wt. % of a photoinitiator (IRGACURE, Ciba Geigy) and 1 wt. % BHT, dissolved in anisole (2 wt. %) and then spun at 3500 revolutions per minute on to a glass plate which had been coated with PVA (PVA=polyvinyl alcohol) and rubbed. The layer was dried at 90° C. on a heating block, then irradiated with xenon light (e.g. for 3 minutes) in a vacuum oven under a vacuum at 90° C. A parallel orientated nematic layer having a layer thickness of 200 mm and having a double refraction (Dn) of 0.15 was produced. This layer functions as an optical retarder.

EXAMPLE 8

1,6-Hexylene bis[2,5-bis(4-[6-acryloyloxyhexyloxy)]phenylcarbonyloxy)benzoic acid ester] was treated with 1 wt. % IRGACURE and 1 wt. % BHT, dissolved in anisole (2 wt. %) and then spun at 3500 revolutions per minute onto a glass plate. The glass plate had previously been coated with methacryloyloxyethyl 3 -(E)-[4-cyano-4'-biphenyl] acrylate and then irradiated with linear polarized light. Thereby, a predetermined structure had been inscribed photolithographically by means of a mask in the (PPN) layer. The new layer (on the PPN layer) was dried at 90° C. on a heating block, then irradiated with xenon light in a vacuum oven under a vacuum at 90° C. The inscribed original structure remained and was copied faithfully from the new network. A clear double refraction (Dn) was recognizable. This layer functions as a structural optical retarder.

We claim:

1. A compound of the formula

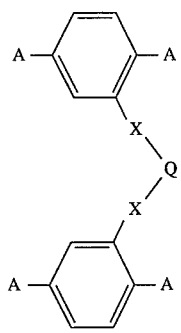

I wherein

A is a cross-linkable mesogenic residue of the formula

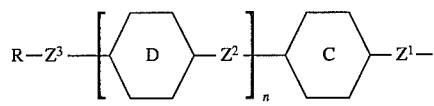

II wherein rings C and D each independently are 1,4-phenylene, which is optionally substituted with halogen, methyl and/or cyano, pyridine-2,5-diyl, pyrimidine-2,5-diyl, trans-1,4-cyclohexylene or trans-1,3-dioxane-2,5-diyl;

$Z^1$ is —$CH_2CH_2$—, —$CH_2O$—, —COO—, —OOC—, —$(CH_2)_4$— or —$(CH_2)_3O$—;

$Z^2$ is a single bond, —$CH_2CH_2$—, —$CH_2O$—, —$OCH_2$—, —COO—, —OOC—, —$(CH_2)_4$—, —$O(CH_2)_3$— or —$(CH_2)_3O$—;

$Z^3$ is —$(CH_2)_m$—, —$(CH_2)_mO$—, —$O(CH_2)_m$—, —$(CH_2)_mCOO$—, —$OOC(CH_2)_m$—, —$(CH_2)_mOOC$— or —$COO(CH_2)_m$—;

n is 0 or 1;

m is a whole number of 1 to 16;

R is acrylate, methacrylate, acryloyloxy, methacryloyloxy, vinyloxy or epoxy;

X is a single bond, —COO—, —$CH_2O$—, —CONH—, or —C=N—; and

Q is n-alkylene, c-alkylene, 1,4-phenylene, 4,4'-biphenylene or 2,6-naphthylene.

2. The compound according to claim 1, wherein rings C and D each independently are phenylene, which is unsubstituted or substituted with fluorine, pyridine-2,5-diyl, pyrimidine-2,5-diyl or trans-1,4-cyclohexylene;

$Z^1$ is —$CH_2O$—, —COO— or —OOC—; and $Z^2$ is a single bond, —$CH_2CH_2$—, —$CH_2O$—, —$OCH_2$—, —COO— or —OOC—.

3. A compound of the formula

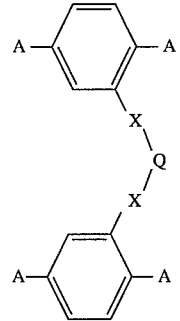

wherein the mesogenic residue A is a residue of the formula

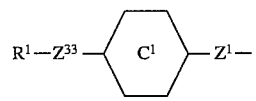

II-a wherein $R^1$ is acrylate, methacrylate, vinyloxy or epoxy;

$Z^{33}$ is —$(CH_2)_{m'}$—, —$(CH_2)_{m'}O$—, —$(CH_2)_{m'}COO$— or —$(CH_2)_{m'}OOC$—;

m' is a whole number of 4 to 12;

ring C is 1,4-phenylene, which is optionally substituted with halogen, or trans-1,4-cyclohexylene;

$Z^1$ is —$CH_2CH_2$—, —$CH_2O$—, —COO—, —OOC—, —$(CH_2)_4$— or —$(CH_2)_3O$—;

X is a single bond, —COO—, —$CH_2O$—, CONH—, or —C=N—; and

Q is n-alkylene, c-alkylene, 1,4-phenylene, 4,4'-biphenylene or 2,6-naphthylene.

4. The compound of claim 1, selected from the group

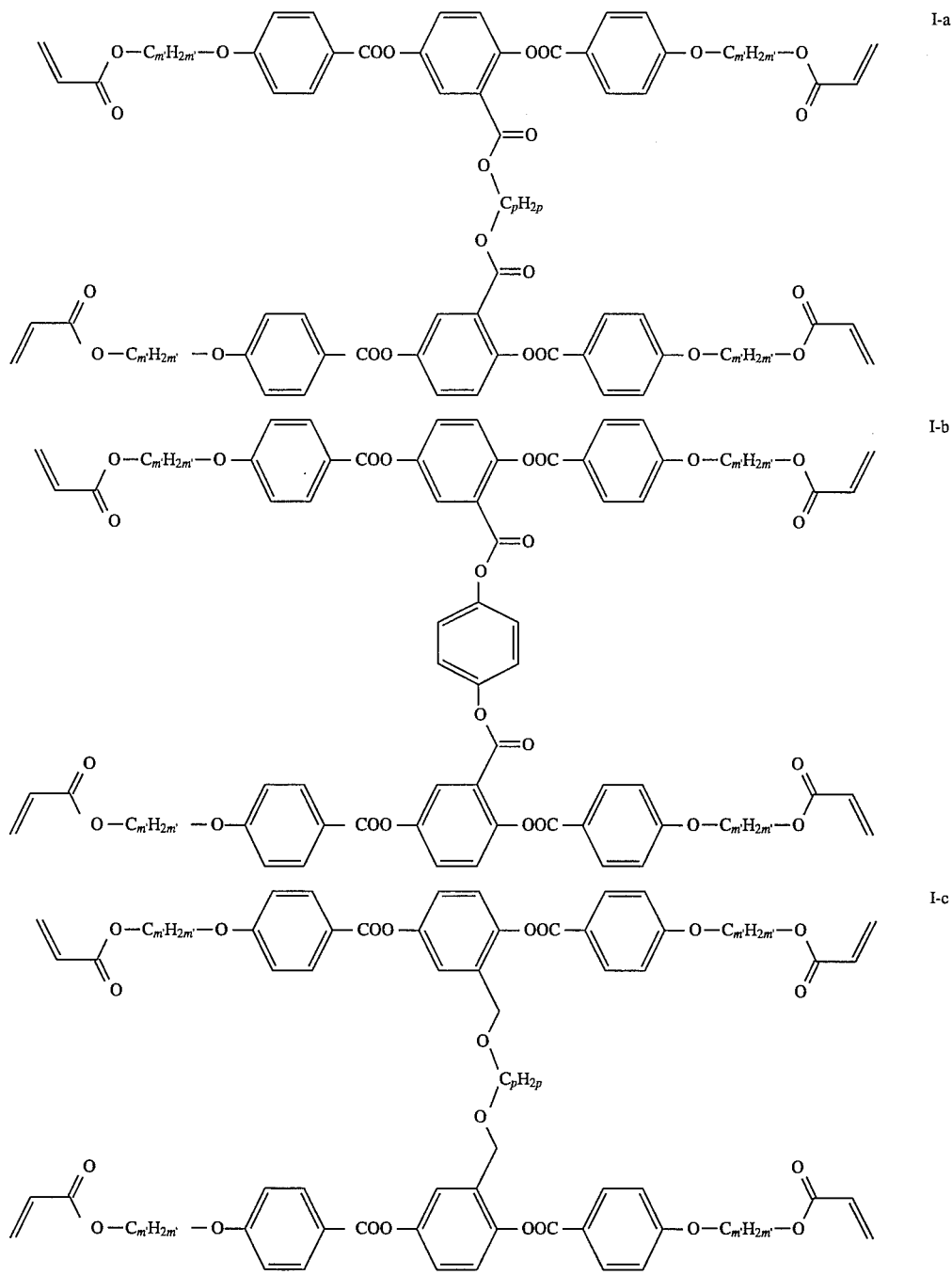

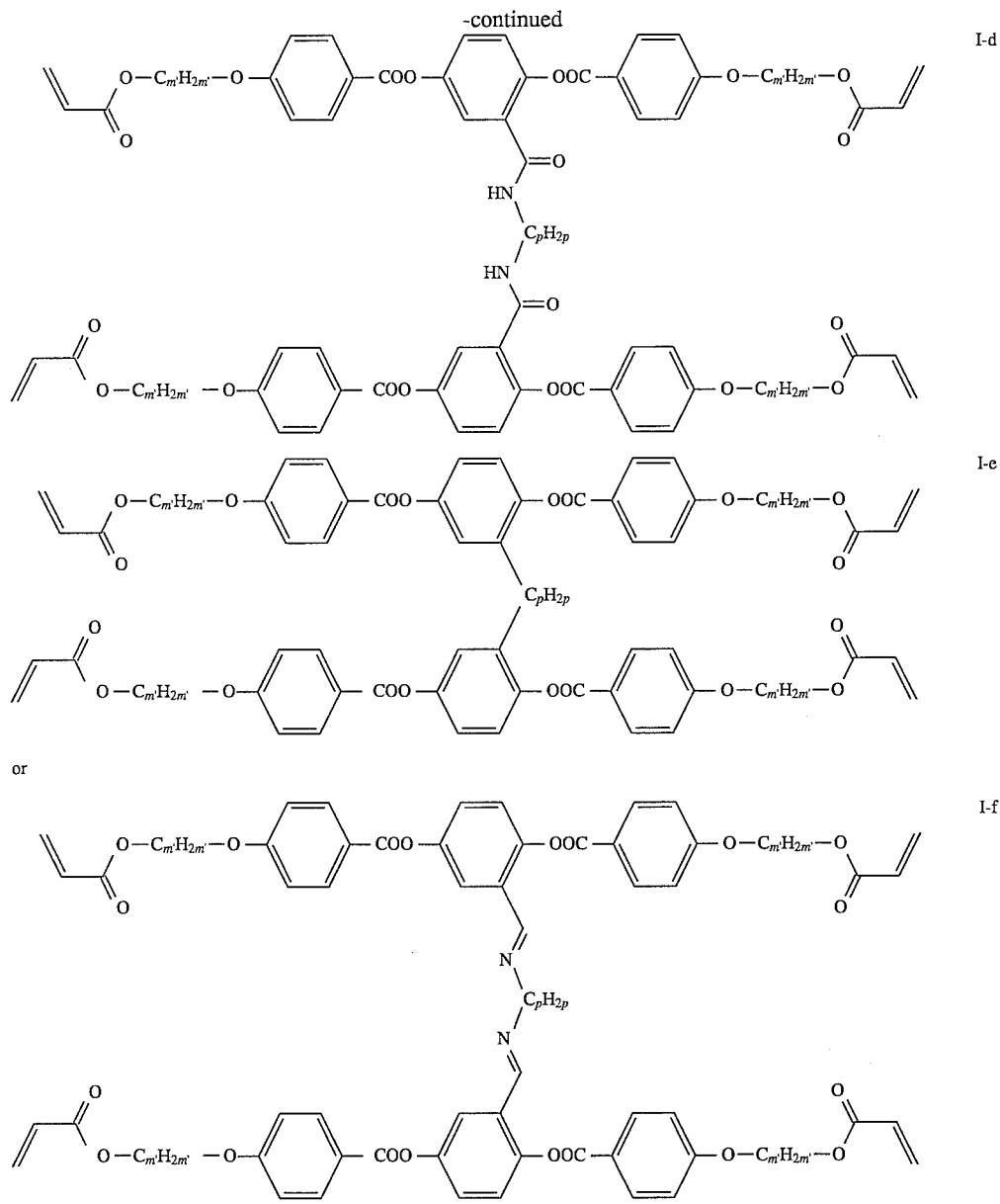

wherein m' is a whole number of 4 to 12 and p is a whole number of 2 to 12.

5. A cross-linkable, liquid crystalline mixture comprising a compound of formula I

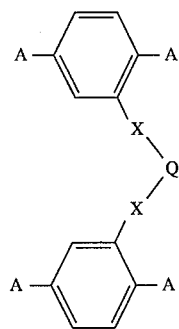

wherein

A is a cross-linkable mesogenic residue of the formula

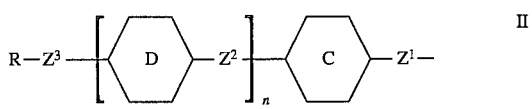

wherein rings C and D each independently are 1,4-phenylene, which is optionally substituted with halogen, methyl and/or cyano, pyridine-2,5-diyl, pyrimidine-2,5-diyl, trans-1,4-cyclohexylene or trans-1,3-dioxane-2,5-diyl;

$Z^1$ is —$CH_2CH_2$—, —$CH_2O$—, —COO—, —OOC—, —$(CH_2)_4$— or —$(CH_2)_3O$—;

$Z^2$ is a single bond, —$CH_2CH_2$—, —$CH_2O$—, —$OCH_2$—, —COO—, —OOC—, —$(CH_2)_4$—, —$O(CH_2)_3$— or —$(CH_2)_3O$—;

$Z^3$ is $-(CH_2)_m-$, $-(CH_2)_mO-$, $-O(CH_2)_m-$, $-(CH_2)_mCOO-$, $-OOC(CH_2)_m-$, $-(CH_2)_mOOC-$ or $-COO(CH_2)_m-$;

n is 0 or 1;

m is a whole number of 1 to 16;

R is acrylate, methacrylate, acryloyloxy, methacryloyloxy, vinyloxy or epoxy;

X is a single bond, $-COO-$, $-CH_2O-$, $-CONH-$, or $-C=N-$; and

Q is n-alkylene, c-alkylene, 1,4-phenylene, 4,4'-biphenylene or 2,6-naphthylene.

6. The cross-linkable, liquid crystalline mixture according to claim 5, further comprising at least one compound selected from the group consisting of

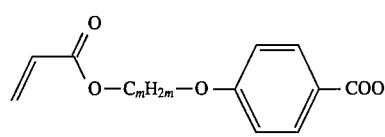
III

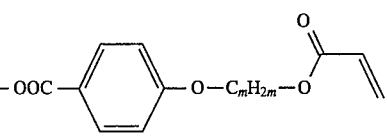
V

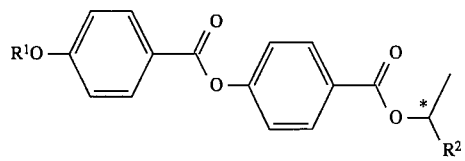
IV

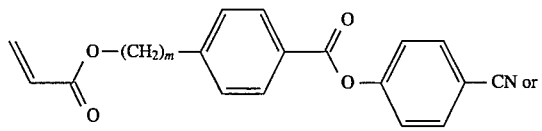
VI

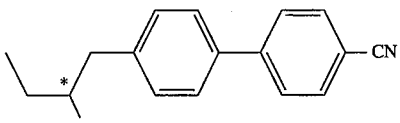

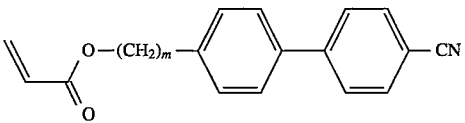
VII wherein $R^1$ and $R^2$ each independently are alkyl or alkenyl with 2 to 12 carbon atoms; X is hydrogen, lower alkyl, fluorine, bromine, chlorine or cyano; and m is a whole number of 1 to 16.

* * * * *